United States Patent [19]
Houghton et al.

[11] 3,944,558
[45] Mar. 16, 1976

[54] FLUOROCARBON DERIVATIVES OF PYRIDINE

[75] Inventors: Leonard Eric Houghton; John Hutchinson, both of Runcorn, England

[73] Assignee: Imperial Chemical Industries Limited, London, England

[22] Filed: Dec. 18, 1972

[21] Appl. No.: 316,088

[30] Foreign Application Priority Data
Jan. 13, 1972   United Kingdom................. 1597/72

[52] U.S. Cl................. 260/297 R; 71/94; 252/102; 252/117; 252/542; 424/263; 260/294.8 F; 260/290 H
[51] Int. Cl.²........................................ C07D 213/26
[58] Field of Search.... 260/290 HL, 297 R, 295.5 R

[56] References Cited
UNITED STATES PATENTS
3,534,056   10/1970   Mailey et al..................... 260/295.5

OTHER PUBLICATIONS
Chemical Abstracts, Vol. 79, abst. no. 115451 (1973) (Abst. of German Offen. No. 2,301,551).

*Primary Examiner*—John D. Randolph
*Attorney, Agent, or Firm*—Cushman, Darby & Cushman

[57] ABSTRACT

Compounds having the general formula $[C_nF_{2n-1}(HF)_x](C_5H_4N)O$ wherein $n$ is an integer from 3 to 20 and $x$ is 0 or 1, the group $C_5H_4N$ is a pyridine nucleus and 0 is an oxygen atom covalently attached to a carbon atom of the nucleus.

12 Claims, No Drawings

FLUOROCARBON DERIVATIVES OF PYRIDINE

This invention relates to novel compounds containing highly fluorinated aliphatic groups.

According to the present invention we provide a compound having the general formula $[C_nF_{2n-1}(HF)_x](C_5H_4N)O$ wherein $n$ is an integer from 3 to 20 and $x$ is 0 or 1, the group $C_5H_4N$ is a pyridine nucleus and O is an oxygen atom covalently attached to a carbon atom of the nucleus.

In one general form of the invention the oxygen atom covalently links the pyridine nucleus $(C_5H_4N)$ with the rest of the structure which is the fluorocarbon portion $(C_nF_{2n-1}(HF)_x)-$. The oxygen atom preferably is linked in the 3-position of the pyridine nucleus for these oxypyridine derivatives but it may be in the 2- or the 4-position if desired. Alternatively the oxygen atom may also be covalently attached to the pyridine nucleus by a double bond and in this form the ring is in a quinonoid form

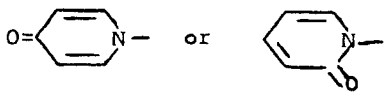

Those oxypyridine derivatives having quinonoid structures are formed when the oxygen atom is in the 2- or 4-positions of the nucleus, and in those cases the fluorocarbon portion is attached directly to the nitrogen atom of the nucleus.

According to a preferred form of the invention we provide a compound having the formula $C_nF_{2n-1}-O(C_5H_4N)$ wherein $n$ is an integer from 3 to 20, the group $C_5H_4N$ is a pyridine nucleus attached to the $C_nF_{2n-1}$ group by an ether oxygen.

The fluorocarbon portion of the structure when $x$ is zero may be a perfluoroalkenyl structure $C_nF_{2n-1}$ of branched or straight-chain skeleton in which the double bond is preferably attached to a carbon atom adjacent to the link to the pyridine nucleus. These are especially preferred forms of the invention and the fluorocarbon portion is conveniently derived from a branched oligomer of tetrafluoroethylene, preferably an oligomer containing 8, 10 or 12 carbon atoms that will produce compounds in which the value of $n$ is 8, 10 or 12.

Alternatively $x$ may be unity and the fluorocarbon structure is then a highly-fluorinated alkyl structure containing one hydrogen atom. The carbon atom carrying the hydrogen atom is preferably a beta-carbon atom relative to the link to the pyridine nucleus. The preferred structure for this form of highly-fluorinated alkyl group is thus $-CF_2CFHC_{n-2}F_{2n-3}$ in which $n$ is from 3 to 20, preferably 3 to 6, and the shortest group $-CF_2CFHCF_3$ is the especially preferred form.

The compounds of this invention may be prepared by reactions between perfluorocarbon compounds containing unsaturated groups and hydroxy pyridines. The unsaturated groups in the perfluorocarbon compounds may be terminal. (e.g. perfluorovinyl) or internal groups, and may include either those containing a fluorine on the double bond (e.g. in tetrafluoroethylene pentamer) as well as those internal double bonds which are fully substituted with perfluoroalkyl groups (e.g. in tetrafluoroethylene tetramer).

The reaction may be carried out in the presence of a proton acceptor for example a base which may be organic, preferably a tertiary amine; or inorganic, preferably a carbonate or silicate of an alkali-metal. Alternatively the proton acceptor may be reacted with the hydroxy pyridine prior to the addition of perfluorocarbon compound, for example an alkali-metal derivative of the hydroxy pyridine may be prepared and subsequently reacted with the perfluorocarbon compound in order to product the compounds of this invention.

The reaction may be conducted in a suitably inert, preferably a polar aprotic, solvent, for example a ketone, an N,N-dimethyl carboxylic amide or a dialkyl sulphoxide; dimethyl sulphoxide, methyl ethyl ketone and dimethylformamide are the preferred solvents.

The compounds $[C_nF_{2n-1}(HF)_x](C_5H_4N)O$ containing a perfluoroaklenyl group are useful surface-active compounds for the treatment of surfaces, for example porous surfaces and especially paper or textile surfaces. The perfluoroalkenyl group imparts to such surfaces a change of character, for example a lowering of surface-free energy which confers on the surface a degree of repellency to organic molecules. Thus surfaces treated with the compounds of this invention have a higher degree of oil-repellency than before treatment.

In addition to the general surface-active properties described above one class of compounds of this invention namely those having the structure

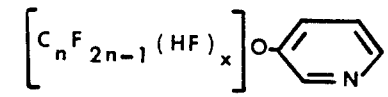

are useful intermediates in the preparation of compounds having a further series of useful properties, i.e. compounds containing a cation having the general formula

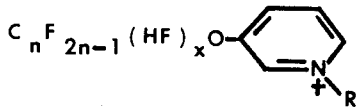

where R is an alkyl group in conjunction with an an anion.

The anion may be any anion which does not adversely affect the surface-active properties of the cation for example halide, sulphate, phosphate, an organic acid anion (e.g. alkyl sulphate) or mixtures thereof.

These compounds may be prepared by quaternisation of the nitrogen atoms of the pyridine nucleus with conventional reagents, for example with dialkyl sulphates, alkyl halides preferably iodides or alkyl esters of aryl sulphonic acids, especially those in which the alkyl group is a lower alkyl group $C_1$–$C_5$.

Such salts are water-soluble compounds useful as cationic surfactants in aqueous systems and biocidal compounds for example as anti-bacterial compounds or potentiators for other known anti-bacterial compounds such as phenolics, hydrochlorites, biguanides, and hydrocarbon quaternaries as described in our co-pending UK Application No. 15790/71 (published Belgian Pat. No. 783630).

The compounds useful as intermediates as hereinbefore described have an advantage over many other compounds formed from perfluoro compounds and an aromatic ring, in that only one chemical step is required to convert to a material having a hydrophilic group and which possesses appreciable surface activity and often water solubility.

As an alternative to the quaternisation step the nitrogen may be oxidised and amine oxides may be made. These materials also have useful properties in aqueous solutions especially as additives to detergent, hypochlorite bleach or other cleaning compositions.

The compounds containing a quinonoid pyridine nucleus also tend to have some biochemical reactivity and therefore these compounds are useful as insecticides, fungicides or herbicides without further chemistry being performed on them.

The invention is illustrated but in no way limited by the following examples:

EXAMPLE 1

To a stirred mixture of tetrafluoroethylene pentamer (500 g, 1 m) anhydrous potassium carbonate (138 g, 1 m) in dimethyl sulphoxide (1 liter), 3-hydroxy pyridine (95 g, 1 m) in dimethyl sulphoxide was added during 20 minutes. The reaction was conducted by stirring the mixture at 25°C for 4 hours. On standing, the mixture separated into two layers. The lower layer was removed, washed with water, dried and distilled under vacuum to yield 506 g of a colourless liquid boiling at 75°C at 2.5 mm Hg.

Infra-red analysis showed absorption peaks at 1570, 1470, 1430 cm$^{-1}$ (C=C and C=N vibrations) and 1237, 1180 cm$^{-1}$ (C—F vibrations).

Mass spectrum of the product revealed a molecular ion at M/e 575 corresponding to the expected molecular formula $C_{15}H_4F_{19}ON$ whilst the fluorine nuclear magnetic resonance and proton nuclear magnetic resonance spectra were fully consistent with the structure

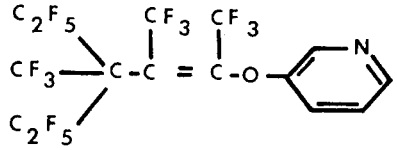

By elemental analysis the product was found to contain 31.43% carbon. 61.33% fluorine, 0.75% hydrogen and 2.67% nitrogen. ($C_{15}F_{19}H_4NO$ requires carbon 31.35%, fluorine 62.8%, hydrogen 0.76% and nitrogen 2.44%).

EXAMPLE 2

An ethereal solution of the pyridyl ether produced in Example 1 (115g, 0.2 m) treated with dimethyl sulphate (26g, 0.2 m) deposited white crystals of the methosulphate quaternary salt

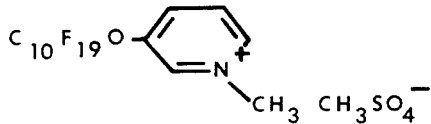

on standing. The quaternary salt was observed to have a melting point of 95°C to 100°C and aqueous solutions gave surface tension values of 23.1, 36.2, 52.8 and 61.3 dynes/cm at 1%, 0.1%, 0.01% and 0.001% concentrations respectively.

EXAMPLE 3

An autoclave (300 ml) charged with 3-hydroxy pyridine (7.1g), potassium carbonate (15g), and methylethylketone (80 ml) was purged with nitrogen, sealed and pressurised with hexafluoropropene. An exothermic reaction ensued and the pressure fell. The vessel was repressurised successively until a drop in pressure no longer occurred. The reaction mixture was filtered and distilled. A fraction boiling at 60°C to 66°C at 7 mm (12g) was collected and shown by mass spectrometry to have parent molecular ions at M/e 245 and 225.

Infra-red and nuclear magnetic resonance spectroscopic analysis demonstrated the product to be a mixture of I. $CF_3CFHCF_2O(C_5H_4N)$
II. trans $CF_3CF=CFO(C_5H_4N)$ and
III. cis $CF_3CF=CFO(C_5H_4N)$ The weight ratio of these components I:II:III in the product was estimated to be 20:2:1. Significant absorption peaks in the infra-red spectrum of the mixed product occurred at 6.80, 7.00, 7.23, 7.77, 8.4 (broad), 8.97, 9.78, 9.88, 10.86. 11.14, 11.41, 11.70, 12.12, 12.37, 13.14, 13.30, 14.10, 14.27μm wavelengths.

EXAMPLE 4

A flask fitted with a vibro-stirrer was connected through a condenser to a manometer, a hexafluoropropene supply and a vacuum pump. The flask was charged with methylethylketone (200 ml), potassium carbonate (22g), 4-hydroxypyridine (10g), cooled to −20°C, pumped out then repressurised to atmospheric pressure with hexafluoropropene. Stirring was commenced and as the pressure fell, hexafluoropropene was allowed into the system to maintain approximately one atmosphere pressure. The vessel temperature during the reaction rose to about −15°C. When no more hexafluoropropene was being taken up, the reaction mixture was filtered and the solvent was distilled off at atmospheric pressure. The residue was distilled at reduced pressure and a main fraction (11.6g, 130°–134°C/20 mm) was collected and shown by infra-red, nuclear magnetic resonance and mass spectrometry (parent molecular ions M/e 245 and 225) to be a mixture of

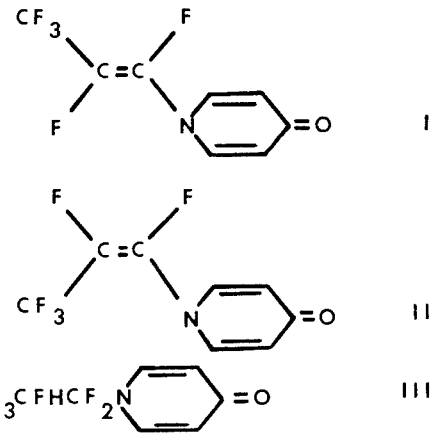

The ratio of these three components I:II:III in the product was estimated to be 3.7:3.2:1. Significant absorption peaks in the infra-red specturm occurred at 3.25, 5.66, 5.99, 6.18, 7.26, 7.59, 8.26, 8.41, 8.62, 9.12, 9.44, 10.77, 11.70, 13.42μm wavelength.

EXAMPLE 5

A reaction between 2-hydroxypyridine and hexafluoropropene was carried out as described for the reaction between hexafluoropropene and 4-hydroxypyridine. The product (19.4g, 69°–70°C/2–3 mm) was identified by nuclear magnetic resonance, infra-red and mass spectrometry (parent molecular ions at M/ε 225 and 245) as a mixture of

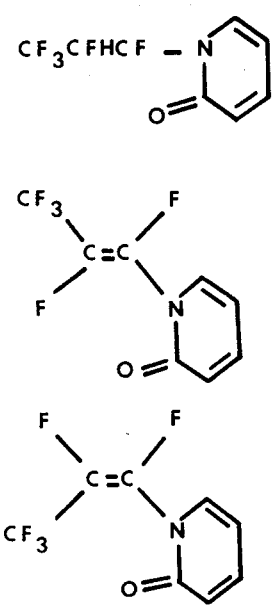

I, II and III were present in the ratio 21:12:10. Significant absorption in the infra-red spectra occurred at 5.90, 6.19, 6.48, 7.30, 7.66, 7.82, 8.35, 8.60, 8.79, 9.50, 10.12, 10.63, 11.09, 11.50, 11.70, 11.86, 12.20, 13.16, 13.44, 13.60, 13.70, 14.20μm wavelength.

EXAMPLE 6

Tetrafluoroethylene tetramer (120g, 0.3 m) was added dropwise, with stirring, to a solution of 3-hydroxypyridine (31.3g, 0.33 m) in dimethylsulphoxide (300 ml) containing triethylamine (41.4 ml, 0.3 m) during 1 hour. The mixture was stirred at 25°C for an additional 3 hours and then allowed to separate into two layers.

The lower layer was washed with water, dried and distilled to yield a colourless liquid, boiling point 70°C to 72°C at 5 mm Hg.

Spectroscopic measurements on the compound were fully consistent with the formula

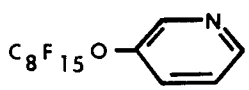

By elemental analysis the product was found to contain carbon 33.17%, hydrogen 0.79%, nitrogen 2.96%, fluorine 56.88%. ($C_{13}F_{15}H_4NO$ requires carbon 32.85%, hydrogen 0.84%, nitrogen 2.95% and fluorine 60%).

The quaternary methosulphate surfactant $C_8F_{15}OC_5H_4N^+CH_3(CH_3SO_4^-)$ was readily prepared in quantitative yield as a white waxy solid (melting point 87°C) by treating an ethereal solution of the 3-tetramer ether of pyridine with dimethylsulphate.

Aqueous solutions of this compound had the following surface tensions: 21.8, 39.0, 57.8, 63.7 dynes/cm at concentrations of 1%, 0.1%, 0.01%, 0.001% respectively.

EXAMPLE 7 a. To a stirred mixture of tetrafluoroethylene pentamer (100g, 0.2 m), 3-hydroxypyridine (20g, 0.21 m) and dry dimethylformamide (100 ml) was slowly added with stirring a solution of methylamine (22g, 0.21 m) in dimethylformamide (100 ml). Stirring was continued for 48 hours at room temperature after which the reaction mixture was poured into dilute acid and a lower layer which formed on standing for a few minutes was run off. This lower layer was dissolved in methylene chloride, washed with water, dried and then the solvent was removed by distillation. The residue was distilled under reduced pressure, 98°–110°C at 3 mm, 95g. This distillate was examined by g.l.c. and found to consist of three components. Further examination by mass spectrometry and $19_F$ nuclear magnetic resonance spectrometry showed that these components were isomers of the pyridyl ether, $C_{10}F_{19}O(C_5H_4N)$. The isomers had the structures

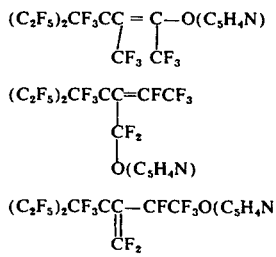

The molar ratio of these three was approximately 2:1:1.

b. The experiment of Example 7(a) was repeated except that the reaction mixture was stirred for 4 hours only at room temperature and the product separated in the same manner as described in Example 7(a) immediately after the 4 hours reaction period. The ratio of the isomers I: II: III in this case was 8:1:1.

EXAMPLE 8

The experiment described in Example 7(b) was repeated using acetonitrile as the solvent. The product in this case was almost exclusively isomer I, with only a trace of II and III.

EXAMPLE 9

When a mixture of the isomers of $C_{10}F_{19}OC_5H_4N$ (730g, 1.27m) produced by Example 7(a) or 7(b) and dimethylsulphate (197g, 1.56 m) in methylene chloride (1.2 liter) was gently refluxed for 5 hours, the isomeric methosulphates (791g) were precipitated. They were all shown to have the formula $C_{10}F_{19}O(C_5H_4N^+CH_3)$ $(CH_3^-SO_4)$ and the proportion of each isomer of the $C_{10}F_{19}$ group present remained unchanged before and after the quaternisation of the nitrogen.

What we claim is:

1. A compound having the general formula

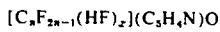

wherein
 $n$ is an integer from 3 to 20
 $x$ is 0 or 1
 the group ($C_5H_4N$) is a pyridine nucleus and
 O is an ether linkage oxygen atom covalently attached to the three position carbon atom of the pyridine nucleus and linking the $[C_nF_{2n-1}(HF)_x]$ group.

2. A compound as claimed in claim 1 wherein $x$ is zero and the formula is

3. A compound as claimed in claim 1 wherein the group $C_nF_{2n-1}$ is a branched perfluoroalkenyl group derived from an oligomer of tetrafluoroethylene.

4. A compound as claimed in claim 3 wherein in the group $C_nF_{2n-1}$ $n$ is 8, 10 or 12.

5. A compound as claimed in claim 1 wherein the pyridine nucleus is quaternised and forms a cationic surface-active agent.

6. A cationic surface-active agent having a cation of the structure

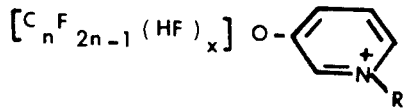

wherein
 $n$ is an integer from 3 to 20
 $x$ is 0 or 1
 R is an alkyl group
in conjunction with an anion.

7. A cationic surface-active agent as claimed in claim 6 wherein the alkyl group R contains up to five carbon atoms.

8. A process for the preparation of oxypyridine derivatives of perfluoroolefines comprising contacting a perfluoroolefine with a hydroxy pyridine in the presence of a proton acceptor and a polar aprotic solvent.

9. A process as claimed in claim 8 wherein the proton acceptor is a base.

10. A process as claimed in claim 9 wherein the base is an organic tertiary amine.

11. A process as claimed in claim 9 wherein the base is a carbonate or silicate of an alkalimetal.

12. A compound as claimed in claim 1 of the formula

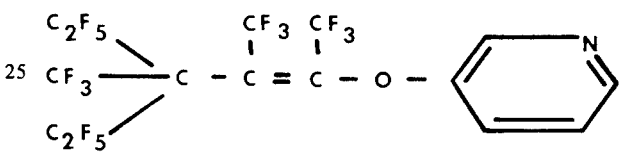

* * * * *